United States Patent
Bahl

(10) Patent No.: US 7,049,060 B2
(45) Date of Patent: May 23, 2006

(54) HCV ANTI-CORE MONOCLONAL ANTIBODIES

(75) Inventor: Chander Bahl, Flemington, NJ (US)

(73) Assignee: Ortho-Clinical Diagnostics, Inc., Rochester, NY (US)

(*) Notice: Subject to any disclaimer, the term of this patent is extended or adjusted under 35 U.S.C. 154(b) by 338 days.

(21) Appl. No.: 10/268,561

(22) Filed: Oct. 10, 2002

(65) Prior Publication Data

US 2003/0148333 A1 Aug. 7, 2003

Related U.S. Application Data

(60) Provisional application No. 60/337,453, filed on Nov. 5, 2001.

(51) Int. Cl.
*C12Q 1/70* (2006.01)
*C12N 5/06* (2006.01)
*C07K 16/10* (2006.01)

(52) U.S. Cl. .......................... 435/5; 435/331; 435/339; 530/388.3

(58) Field of Classification Search .................. 435/5, 435/331, 339; 530/388.3
See application file for complete search history.

(56) References Cited

U.S. PATENT DOCUMENTS

| 5,871,904 A | * | 2/1999 | Kashiwakuma et al. | ....... 435/5 |
| 2002/0192639 A1 | * | 12/2002 | Chien et al. | ................... 435/5 |
| 2003/0022155 A1 | * | 1/2003 | Budkowska et al. | ........... 435/5 |

FOREIGN PATENT DOCUMENTS

| EP | 0 388 232 A | 9/1990 |
| EP | 0 537 856 A | 4/1993 |
| FR | 2 775 690 A | 9/1999 |
| WO | WO 00 63444 A | 10/2000 |

OTHER PUBLICATIONS

Jolivet–Reynaud et al., HCV Core Immunodominant Region Analysis Using Mouse Monoclonal Antibodies and Human Sera: Characterization of Major Epitopes Useful for Antigen Detection. Journal of Medical Virology 56:300–309, 1998.*
Harlow, Ed and Lane, David: "Antibodies". A Laboratory Manual. 1988, Chapter 6, Cold Spring Harbor Laboratory.
Partial EPO Search Report, dated May 27, 2003, for EPO Appln. No. EP 02 25 7622.

* cited by examiner

*Primary Examiner*—Donna C. Wortman

(57) ABSTRACT

Monoclonal antibodies that specifically bind to HCV core antigen. Also provided are hybridoma cell lines which secrete these antibodies, methods for making and using these antibodies, including kits that include these antibodies.

4 Claims, No Drawings

HCV ANTI-CORE MONOCLONAL ANTIBODIES

This application claims the benefit of U.S. Provisional Application Ser. No. 60/337,453, filed Nov. 5, 2001 (now abandoned).

BACKGROUND OF THE INVENTION

An estimated 170 million people worldwide have been infected by hepatitis C virus (HCV). In the next few years, the number of U.S. deaths for HCV-caused liver disease and cancer may overtake deaths caused by Acquired Immune Deficiency Syndrome (AIDS).

The transmission of HCV seems to require blood-to-blood contact. Carrying a single strand of ribonucleic acid (RNA), HCV contains just one gene, coding for a polyprotein that is subsequently cleaved into at least 10 functional proteins. Clearly, the ability to test the blood supply for HCV is of great importance. A sensitive assay that can detect infection at an early stage. Detection of both HCV antigens and antibodies in a single assay would therefore be advantageous.

HCV core detection assays capture HCV antigen from the HCV infected specimens on a solid phase coated with anti-core monoclonal antibodies. The captured core protein is detected by a binding reaction with an anti-core monoclonal antibody labeled with enzyme using standard immunoassay technology. Availability of good monoclonal antibodies to multiple epitopes of HCV core antigen will increase the sensitivity of HCV antigen detection assays. For one thing, multiple antibodies increase the efficiency of the capture of the HCV antigen from specimens onto the solid phase. Second, using multiple antibodies for detection increases the sensitivity of the system by providing a cumulative higher signal. Another advantage is that the use of multiple epitope recognizing antibodies in assays enables the assays to detect specimens infected with different genotypes of the HCV virus.

SUMMARY OF THE INVENTION

The present invention describes a library of monoclonal antibodies directed against various regions of the HCV core protein. These antibodies recognize ten (10) different epitopes in the HCV core region and are spread throughout the core protein. The epitopes recognized by these monoclonal antibodies are five to eight (5–8) amino acids ("aa") long. These antibodies in individual pairs or multiple pairs are useful in detecting HCV core protein in patients infected with HCV. Specifically, these antibodies are advantageous in detecting HCV in blood from infected humans. Finally, these antibodies along with properly tailored recombinant proteins can be used for the simultaneous detection of HCV core protein and ant-HCV antibodies.

We have developed a number of anti-HCV core monoclonal antibodies. These antibodies have unique properties in that they recognize short sequences, in the region of HCV core that does not have major epitopes recognized by human anti-HCV antibodies. These antibodies can be useful reagents in detecting HCV core antigen in blood specimens from individuals infected with HCV. The recognition of short epitopes by these monoclonal antibodies and the location of these sequences in the core region of HCV make these monoclonal antibodies very useful in the development of a HCV antigen/antibody combination assay. For the combination assay these monoclonal antibodies are used in combination with core antigen that has been modified to eliminate the ability of these antigens to bind to these monoclonal antibodies but maintain their ability to bind human anti-HCV antibodies. Therefore, the HCV core proteins used to capture the antibodies present in infected serum will not react with the HCV core monoclonal antibodies used in the test to simultaneously capture the antigens present in the infected serum. A combination assay can detect HCV infection earlier than the currently employed HCV antibody assay.

DETAILED DESCRIPTION OF THE INVENTION

The effectiveness and advantages of the invention are further illustrated by the following examples.

EXAMPLE 1

Immunogens

Immunogens used for raising the antibodies were a full length core recombinant protein ("FLC")(amino acids (aa) 1–191); c22-3, HCV core protein expressed in yeast as an SOD fusion protein (aa 1–120); and large synthetic peptides, such as ODS243(aa 70–110); and keyhole limpet hemacynin (KLH) conjugated 15 mer peptides containing sequences from HCV core antigen.

EXAMPLE 2

Immunizing Protocol

The antibodies were generated using standard procedures. See for example, Ed Harlow and David Lane, Antibodies, A Laboratory Manual, 1988, Cold Spring Harbor, Chapter 6. Mice were immunized with the immunogens described herein. The mice were bled and screened with a number of recombinant proteins and peptides from the HCV core sequence. Pure monoclonal antibodies were prepared by protein A affinity chromatography. The fine specificity of the monoclonal antibodies was determined by binding overlapping octapeptides contained in each of the corresponding 15 mer peptide. Most antibodies were mapped to a 6–8 amino acid region in the HCV core protein sequence.

EXAMPLE 3

Characterization of the Antibodies

The monoclonal antibodies were characterized by ELISA using overlapping synthetic peptides approximately 15 aa long. The antibodies were further characterized for their fine specificity by peptide ELISA using overlapping octapeptides included in the reactive 15 mer peptide. A summary of antibodies generated is included in the following table.

TABLE 1

The table below identifies 15 novel antibodies. The antibodies were screened at every stage of antibody development with microtitrewell plates coated with immunogen. The immunogen used to immunize the mice that produced each strain of monoclonal antibody is identified as one of the following: peptide ODS 243, a large peptide further defined in Example 1; "FLC" means full length core antigen, defined in Example 1; or KLH conjugated core peptide #8, a short peptide, further defined herein. The specificity of each to a numbered peptide is shown and the amino acid sequences of each numbered peptide is identified herein. Furthermore, the epitope to which the antibody specifically binds is included in the last column, defined by the amino acids that encode for the epitope.

The antibodies were deposited on Oct. 24, 2001 with the International Depository Authority: American Type Culture Collection, Manassas, Va. 20110-2209 USA ("ATCC"). The ATCC accession numbers are listed in the first column of the table below.

| ATCC # | AG-FUSION #, clone | IMMUNOGEN | ISOTYPE | SPECIFICITY | AA |
|---|---|---|---|---|---|
| PTA-3811 | ODS243, 7B4F11 | Peptide ODS 243 | IgG2b | HCV core peptide #8 | 77–91 |
| PTA-3803 | ODS243, 1E3D12 | Peptide ODS 243 | IgG2a | HCV core peptide #9 | 86–100 |
| PTA-3802 | ODS243, 7C12C4 | Peptide ODS 243 | IgG2b | HCV core peptide #8 | 77–91 |
| PTA-3813 | core#3, 2A11C6 | FLC | IgG1 | HCV core peptide #11 | 106–120 |
| PTA-3809 | Core#12, 1B7A1 | FLC | IgG1 | HCV core peptide #3 | 29–43 |
| PTA-3805 | Core#13, 5A12G12 | FLC | IgG1 | HCV core peptide #4 | 39–53 |
| PTA-3812 | Core#13, 4H7E7 | FLC | IgG1 | HCV core peptide #5 | 48–62 |
| PTA-3806 | Core#13, 12F4A11 | FLC | IgG1 | HCV core peptide #6 | 58–72 |
| PTA-3804 | Core#13, 14D12A12 | FLC | IgG1 | HCV core peptide #7 | 67–81 |
| PTA-3807 | c22-8#4, 6D8E8 | KLH Conjugated core peptide #8 | IgG1 | HCV core peptide #8 | 77–91 |
| PTA-3800 | Core#12, 4G10G6 | FLC | IgG2b | HCV core peptide #10 | 96–110 |
| PTA-3801 | Core#13, 6E7E1 | FLC | IgG2a | HCV core peptide #11 | 106–120 |
| PTA-3810 | Core#13, 11D12A6 | FLC | IgG2b | HCV core peptide #11 | 106–120 |
| PTA-3808 | Core#13, 14B7C3 | FLC | IgG3 | HCV core peptide #11 | 106–120 |
| PTA-3799 | Core#12, 4A6H3 | FLC | IgG1 | HCV core peptide #16 | 156–170 |

TABLE 2

The table below shows HCV core synthetic peptides.

| Peptide ID # | Amino Acid Sequence | HCV protein AA Location | |
|---|---|---|---|
| 0 | MSTNPKPQKKNKRNT | 1–15 | SEQ ID NO.:1 |
| 1 | KNKRNTNRRPQDVKF | 10–24 | SEQ ID NO.:2 |
| 2 | QDVKFPGGGQIVGGV | 20–34 | SEQ ID NO.:3 |
| 3 | QIVGGVYLLPRRGPR | 29–43 | SEQ ID NO.:4 |
| 4 | RRGPRLGVRATRKTS | 39–53 | SEQ ID NO.:5 |
| 5 | ATRKTSERSQPRGRR | 48–62 | SEQ ID NO.:6 |
| 6 | PRGRRQPIPKARRPE | 58–72 | SEQ ID NO.:7 |
| 7 | KARRPEGRTWAQPGY | 67–81 | SEQ ID NO.:8 |
| 8 | AQPGYPWPLYGNEGC | 77–91 | SEQ ID NO.:9 |
| 9 | YGNEGCGWAGWLLSP | 86–100 | SEQ ID NO.:10 |
| 10 | WLLSPRGSRPSWGPT | 96–110 | SEQ ID NO.:11 |
| 11 | SWGPTDPRRRSRLNG | 106–120 | SEQ ID NO.:12 |
| 12 | SRLNGKVIDTLTCGF | 116–130 | SEQ ID NO.:13 |
| 13 | LTCGFADLMGYIPLV | 126–140 | SEQ ID NO.:14 |
| 14 | YIPLVGAPLGGAARA | 136–150 | SEQ ID NO.:15 |
| 15 | GAARALAHGVRVLED | 146–160 | SEQ ID NO.:16 |
| 16 | RVLEDGVNYATGNLP | 156–170 | SEQ ID NO.:17 |
| 17 | TGNLPGCSFSIFLLA | 166–180 | SEQ ID NO.:18 |
| 18 | IFLLALLSCLTVPAS | 176–190 | SEQ ID NO.:19 |

TABLE 3

The table below shows the screening of the antibody identified as PTA-3811 with ELISA plates coated with HCV core peptides.

| Peptide ID # | Optical Density in ELISA |
|---|---|
| 0 | 0 |
| 1 | 0.04 |
| 2 | 0 |
| 3 | 0.01 |
| 4 | 0.01 |
| 5 | 0 |
| 6 | 0 |
| 7 | 0.01 |
| 8 | 2.5 |
| 9 | 0 |
| 10 | 0.01 |
| 11 | 0.01 |
| 12 | 0 |
| 13 | 0.01 |
| 14 | 0.01 |
| 15 | 0 |
| 16 | 0.01 |
| 17 | 0.01 |
| 18 | 0.01 |

TABLE 4

Epitope mapping of monoclonal antibody PTA-3811 using overlapping octapeptides.

| Sequence of octapeptides | AA Location | ALU | |
|---|---|---|---|
| (7.9) Biotin-Ahx-TWAQPGYP | 75–82 | 0.57 | SEQ ID NO.:20 |
| (7.10) Biotin-Ahx-WAQPGYPW | 76–83 | 1.05 | SEQ ID NO.:21 |
| (8.1) Biotin-Ahx-AQPGYPWP | 77–84 | 0.61 | SEQ ID NO.:22 |
| (8.2) Biotin-Ahx-QPGYPWPL | 78–85 | 10.84 | SEQ ID NO.:23 |
| (8.3) Biotin-Ahx-PGYPWPLY | 79–86 | 45.89 | SEQ ID NO.:24 |
| (8.4) Biotin-Ahx-GYPWPLYG | 80–87 | 43.03 | SEQ ID NO.:25 |
| (8.5) Biotin-Ahx-YPWPLYGN | 81–88 | 33.81 | SEQ ID NO.:26 |
| (8.6) Biotin-Ahx-PWPLYGNE | 82–89 | 3.11 | SEQ ID NO.:27 |
| (8.7) Biotin-Ahx-WPLYGNEG | 83–90 | 0.27 | SEQ ID NO.:28 |
| (8.8) Biotin-Ahx-PLYGNEGC | 84–91 | 0.3 | SEQ ID NO.:29 |
| (8.9) Biotin-Ahx-LYGNEGCG | 85–92 | 0.42 | SEQ ID NO.:30 |
| (9.1) Biotin-Ahx-YGNEGCGW | 86–93 | 0.49 | SEQ ID NO.:31 |
| (9.2) Biotin-Ahx-GNEGCGWA | 87–94 | 0.6 | SEQ ID NO.:32 |

Monoclonal antibody 7B4F11 reacted with Octapeptides 8.2, 8.3, 8.4, 8.5 in a chemiluminescence ELISA measured in arbitrary light units (ALU). Based on the reactivity of the octapeptides the monoclonal epitope is centered around the sequence PWPL (SEQ ID NO.: 33).

The above examples are meant to illustrate, but not to limit, the scope and spirit of the invention.

It is to be understood that numerous changes and modifications may be made therein without departing from the scope and intent of the invention.

For example, it would be understood by one skilled in the art that all of the monoclonal antibodies disclosed herein can be used individually or as combinations as capture regents or as detecting reagents for the detection of HCV core antigen in a HCV core antigen assay or an HCV antibody/antigen combination assay.

---

What is claimed is:

1. A hybridoma cell line corresponding to the ATCC number selected from the group consisting of PTA-3799, PTA-3800, PTA-3801, PTA-3802, PTA-3803, PTA-3804, PTA-3805, PTA-3806, PTA-3807, PTA-3808, PTA-3809, PTA-3810, PTA-3811, PTA-3812, and PTA-3813.

2. A monoclonal antibody secreted by any one of the hybridoma cell lines claimed in claim 1.

3. Assay kits that contain one or more of the monoclonal antibodies claimed in claim 2.

4. A method for the detection of HCV core antigens comprising:

1) contacting a sample that may contain said HCV core antigens with one or more of the monoclonal antibodies claimed in claim 2; and 2) detecting the presence of immune complexes as an indication of the presence of HCV core antigen.

* * * * *

SEQUENCE LISTING

<160> NUMBER OF SEQ ID NOS: 33

<210> SEQ ID NO 1
<211> LENGTH: 15
<212> TYPE: PRT
<213> ORGANISM: Hepatitis C virus

<400> SEQUENCE: 1

Met Ser Thr Asn Pro Lys Pro Gln Lys Lys Asn Lys Arg Asn Thr
1               5                   10                  15

<210> SEQ ID NO 2
<211> LENGTH: 15
<212> TYPE: PRT
<213> ORGANISM: Hepatitis C virus

<400> SEQUENCE: 2

Lys Asn Lys Arg Asn Thr Asn Arg Arg Pro Gln Asp Val Lys Phe
1               5                   10                  15

<210> SEQ ID NO 3
<211> LENGTH: 15
<212> TYPE: PRT
<213> ORGANISM: Hepatitis C virus

<400> SEQUENCE: 3

Gln Asp Val Lys Phe Pro Gly Gly Gly Gln Ile Val Gly Gly Val
1               5                   10                  15

<210> SEQ ID NO 4
<211> LENGTH: 15
<212> TYPE: PRT

-continued

```
<213> ORGANISM: Hepatitis C virus

<400> SEQUENCE: 4

Gln Ile Val Gly Gly Val Tyr Leu Leu Pro Arg Arg Gly Pro Arg
1               5                   10                  15

<210> SEQ ID NO 5
<211> LENGTH: 15
<212> TYPE: PRT
<213> ORGANISM: Hepatitis C virus

<400> SEQUENCE: 5

Arg Arg Gly Pro Arg Leu Gly Val Arg Ala Thr Arg Lys Thr Ser
1               5                   10                  15

<210> SEQ ID NO 6
<211> LENGTH: 15
<212> TYPE: PRT
<213> ORGANISM: Hepatitis C virus

<400> SEQUENCE: 6

Ala Thr Arg Lys Thr Ser Glu Arg Ser Gln Pro Arg Gly Arg Arg
1               5                   10                  15

<210> SEQ ID NO 7
<211> LENGTH: 15
<212> TYPE: PRT
<213> ORGANISM: Hepatitis C virus

<400> SEQUENCE: 7

Pro Arg Gly Arg Arg Gln Pro Ile Pro Lys Ala Arg Arg Pro Glu
1               5                   10                  15

<210> SEQ ID NO 8
<211> LENGTH: 15
<212> TYPE: PRT
<213> ORGANISM: Hepatitis C virus

<400> SEQUENCE: 8

Lys Ala Arg Arg Pro Glu Gly Arg Thr Trp Ala Gln Pro Gly Tyr
1               5                   10                  15

<210> SEQ ID NO 9
<211> LENGTH: 15
<212> TYPE: PRT
<213> ORGANISM: Hepatitis C virus

<400> SEQUENCE: 9

Ala Gln Pro Gly Tyr Pro Trp Pro Leu Tyr Gly Asn Glu Gly Cys
1               5                   10                  15

<210> SEQ ID NO 10
<211> LENGTH: 15
<212> TYPE: PRT
<213> ORGANISM: Hepatitis C virus

<400> SEQUENCE: 10

Tyr Gly Asn Glu Gly Cys Gly Trp Ala Gly Trp Leu Leu Ser Pro
1               5                   10                  15

<210> SEQ ID NO 11
<211> LENGTH: 15
<212> TYPE: PRT
<213> ORGANISM: Hepatitis C virus
```

```
-continued

<400> SEQUENCE: 11

Trp Leu Leu Ser Pro Arg Gly Ser Arg Pro Ser Trp Gly Pro Thr
1               5                   10                  15

<210> SEQ ID NO 12
<211> LENGTH: 15
<212> TYPE: PRT
<213> ORGANISM: Hepatitis C virus

<400> SEQUENCE: 12

Ser Trp Gly Pro Thr Asp Pro Arg Arg Arg Ser Arg Leu Asn Gly
1               5                   10                  15

<210> SEQ ID NO 13
<211> LENGTH: 15
<212> TYPE: PRT
<213> ORGANISM: Hepatitis C virus

<400> SEQUENCE: 13

Ser Arg Leu Asn Gly Lys Val Ile Asp Thr Leu Thr Cys Gly Phe
1               5                   10                  15

<210> SEQ ID NO 14
<211> LENGTH: 15
<212> TYPE: PRT
<213> ORGANISM: Hepatitis C virus

<400> SEQUENCE: 14

Leu Thr Cys Gly Phe Ala Asp Leu Met Gly Tyr Ile Pro Leu Val
1               5                   10                  15

<210> SEQ ID NO 15
<211> LENGTH: 15
<212> TYPE: PRT
<213> ORGANISM: Hepatitis C virus

<400> SEQUENCE: 15

Tyr Ile Pro Leu Val Gly Ala Pro Leu Gly Gly Ala Ala Arg Ala
1               5                   10                  15

<210> SEQ ID NO 16
<211> LENGTH: 15
<212> TYPE: PRT
<213> ORGANISM: Hepatitis C virus

<400> SEQUENCE: 16

Gly Ala Ala Arg Ala Leu Ala His Gly Val Arg Val Leu Glu Asp
1               5                   10                  15

<210> SEQ ID NO 17
<211> LENGTH: 15
<212> TYPE: PRT
<213> ORGANISM: Hepatitis C virus

<400> SEQUENCE: 17

Arg Val Leu Glu Asp Gly Val Asn Tyr Ala Thr Gly Asn Leu Pro
1               5                   10                  15

<210> SEQ ID NO 18
<211> LENGTH: 15
<212> TYPE: PRT
<213> ORGANISM: Hepatitis C virus

<400> SEQUENCE: 18
```

Thr Gly Asn Leu Pro Gly Cys Ser Phe Ser Ile Phe Leu Leu Ala
1               5                   10                  15

<210> SEQ ID NO 19
<211> LENGTH: 15
<212> TYPE: PRT
<213> ORGANISM: Hepatitis C virus

<400> SEQUENCE: 19

Ile Phe Leu Leu Ala Leu Leu Ser Cys Leu Thr Val Pro Ala Ser
1               5                   10                  15

<210> SEQ ID NO 20
<211> LENGTH: 8
<212> TYPE: PRT
<213> ORGANISM: hepatitis C

<400> SEQUENCE: 20

Thr Trp Ala Gln Pro Gly Tyr Pro
1               5

<210> SEQ ID NO 21
<211> LENGTH: 8
<212> TYPE: PRT
<213> ORGANISM: hepatitis C

<400> SEQUENCE: 21

Trp Ala Gln Pro Gly Tyr Pro Trp
1               5

<210> SEQ ID NO 22
<211> LENGTH: 8
<212> TYPE: PRT
<213> ORGANISM: hepatitis C

<400> SEQUENCE: 22

Ala Gln Pro Gly Tyr Pro Trp Pro
1               5

<210> SEQ ID NO 23
<211> LENGTH: 8
<212> TYPE: PRT
<213> ORGANISM: hepatitis C

<400> SEQUENCE: 23

Gln Pro Gly Tyr Pro Trp Pro Leu
1               5

<210> SEQ ID NO 24
<211> LENGTH: 8
<212> TYPE: PRT
<213> ORGANISM: hepatitis C

<400> SEQUENCE: 24

Pro Gly Tyr Pro Trp Pro Leu Tyr
1               5

<210> SEQ ID NO 25
<211> LENGTH: 8
<212> TYPE: PRT
<213> ORGANISM: hepatitis C

<400> SEQUENCE: 25

Gly Tyr Pro Trp Pro Leu Tyr Gly
1               5

```
<210> SEQ ID NO 26
<211> LENGTH: 8
<212> TYPE: PRT
<213> ORGANISM: hepatitis C

<400> SEQUENCE: 26

Tyr Pro Trp Pro Leu Tyr Gly Asn
1               5

<210> SEQ ID NO 27
<211> LENGTH: 8
<212> TYPE: PRT
<213> ORGANISM: hepatitis C

<400> SEQUENCE: 27

Pro Trp Pro Leu Tyr Gly Asn Glu
1               5

<210> SEQ ID NO 28
<211> LENGTH: 8
<212> TYPE: PRT
<213> ORGANISM: hepatitis C

<400> SEQUENCE: 28

Trp Pro Leu Tyr Gly Asn Glu Gly
1               5

<210> SEQ ID NO 29
<211> LENGTH: 8
<212> TYPE: PRT
<213> ORGANISM: hepatitis C

<400> SEQUENCE: 29

Pro Leu Tyr Gly Asn Glu Gly Cys
1               5

<210> SEQ ID NO 30
<211> LENGTH: 8
<212> TYPE: PRT
<213> ORGANISM: hepatitis C

<400> SEQUENCE: 30

Leu Tyr Gly Asn Glu Gly Cys Gly
1               5

<210> SEQ ID NO 31
<211> LENGTH: 8
<212> TYPE: PRT
<213> ORGANISM: hepatitis C

<400> SEQUENCE: 31

Tyr Gly Asn Glu Gly Cys Gly Trp
1               5

<210> SEQ ID NO 32
<211> LENGTH: 16
<212> TYPE: PRT
<213> ORGANISM: hepatitis C

<400> SEQUENCE: 32

Gly Asn Glu Gly Cys Gly Trp Ala Thr Trp Ala Gln Pro Gly Tyr Pro
1               5                   10                  15
```

```
-continued

<210> SEQ ID NO 33
<211> LENGTH: 4
<212> TYPE: PRT
<213> ORGANISM: hepatitis C

<400> SEQUENCE: 33

Pro Trp Pro Leu
1
```